United States Patent
Chen et al.

(10) Patent No.: US 8,616,208 B2
(45) Date of Patent: Dec. 31, 2013

(54) ORAL APPLIANCE WITH AUTO NEGATIVE PRESSURE CONTROL AND METHOD THEREOF

(75) Inventors: Chung-Chu Chen, Taichung (TW); Chen-Liang Lin, Chiayi (TW); Chen-Ning Huang, Taoyuan County (TW); Tung-Ming Yu, Yilan County (TW)

(73) Assignee: Industrial Technology Research Institute, Hsinchu (TW)

( * ) Notice: Subject to any disclaimer, the term of this patent is extended or adjusted under 35 U.S.C. 154(b) by 1051 days.

(21) Appl. No.: 12/561,364

(22) Filed: Sep. 17, 2009

(65) Prior Publication Data
US 2010/0101583 A1  Apr. 29, 2010

Related U.S. Application Data

(60) Provisional application No. 61/109,239, filed on Oct. 29, 2008.

(51) Int. Cl.
*A61M 16/00* (2006.01)
(52) U.S. Cl.
USPC ............ 128/205.19; 128/204.18; 128/204.21; 128/204.23; 128/206.21; 128/206.24
(58) Field of Classification Search
USPC ............ 128/205.19, 204.18, 204.21, 204.23, 128/204.26, 205.23, 206.21, 206.29
See application file for complete search history.

(56) References Cited

U.S. PATENT DOCUMENTS

| | | | |
|---|---|---|---|
| 4,617,525 A * | 10/1986 | Lloyd | 340/573.1 |
| 5,957,133 A | 9/1999 | Hart | |
| 6,033,326 A | 3/2000 | Lee | |
| 6,494,209 B2 | 12/2002 | Kulick | |
| 6,705,315 B2 * | 3/2004 | Sullivan et al. | 128/204.18 |
| 7,328,698 B2 | 2/2008 | Scarberry et al. | |
| 7,918,222 B2 | 4/2011 | Chen | |
| 7,942,824 B1 * | 5/2011 | Kayyali et al. | 600/538 |
| 2003/0111079 A1 * | 6/2003 | Matthews et al. | 128/204.18 |
| 2005/0115561 A1 | 6/2005 | Stahmann et al. | |
| 2005/0166929 A1 | 8/2005 | Jiang | |
| 2006/0096600 A1 * | 5/2006 | Witt et al. | 128/848 |
| 2007/0277818 A1 * | 12/2007 | Chen | 128/200.24 |
| 2009/0288660 A1 | 11/2009 | Chen et al. | |

FOREIGN PATENT DOCUMENTS

| | | |
|---|---|---|
| TW | 200744551 A | 12/2007 |
| TW | 200949072 A | 12/2009 |
| WO | 2008048471 A1 | 4/2008 |

OTHER PUBLICATIONS

TW Office Action dated Jan. 8, 2013.
English Language Abstract translation of TW200949072 (Published Dec. 1, 2009).

* cited by examiner

*Primary Examiner* — Clinton T Ostrup
(74) *Attorney, Agent, or Firm* — McClure, Qualey & Rodack, LLP

(57) ABSTRACT

A method for automatically controlling negative pressure supplied in oral cavity, for relieving sleep apnea and snoring is provided. The method includes: sensing a physiological signal from the user and outputting the sensed physiological signal; extracting a physiological status based on said sensed physiological signal; and automatically controlling said negative pressure provided to the user's oral cavity based on said physiological status.

21 Claims, 15 Drawing Sheets

ORAL APPLIANCE WITH AUTO NEGATIVE PRESSURE CONTROL AND METHOD THEREOF

This application claims the benefit of U.S. Provisional Application Ser. No. 61/109,239, filed on Oct. 29, 2008, the subject matter of which is incorporated herein by reference.

TECHNICAL FIELD

The present application generally relates to an oral appliance with automatic negative pressure control based bio feedback.

BACKGROUND

Obstructive sleep apnea (OSA), hypopnea, and upper airway resistance syndrome (UARS) are among a variety of known disorders characterized by episodes of complete or partial upper airway obstruction during such as sleep, anesthetization, or post anesthesia. OSA, hypopnea, and UARS cause intermittent interruption of ventilation during sleep with the consequence of potentially severe oxyhemoglobin desaturation. Typically, those afflicted with OSA, hypopnea, and UARS experience repeated, frequent arousal from sleep in response to the oxygen deprivation. The arousals result in sleep fragmentation and poor sleep continuity.

A prior oral device for treatment of obstructive sleep disorders is already disclosed. It is characterized in that the tongue is protected and separated from the teeth when the device is in use. The oral device further comprises a tongue shaped cavity for receiving the tongue. Moreover, a negative pressure is applied directly on the soft tissues of the tongue to hold the tongue within the cavity. However, such negative pressure may cause damage to the soft tissues of the tongue.

Moreover, another prior oral appliance with a negative air supply for reducing sleep apnea and snoring is provided, in which a negative air pressure source expels the air from the oral cavity to pull the tongue and the palate forward so that the upper airway is unobstructed.

Although various devices have been developed to facilitate breathing for those suffering from OSA, hypopnea or UARS by using oral negative pressure, they fail to properly control negative pressure applied to oral cavity.

BRIEF SUMMARY

Embodiments of an oral appliance for automatically control negative pressure supplied in an oral cavity and a method therefore are disclosed. The automatic negative pressure control is based on physiological signals feedback from the user.

An exemplary embodiment provides an oral appliance with automatic negative pressure control, comprising: a sensing unit, for sensing a physiological signal from a user and outputting said sensed physiological signal; a physiological status extraction unit, coupled to said sensing unit, for extracting a physiological status based on said sensed physiological signal from said sensing unit; a negative pressure source, for providing a negative pressure; an oral interface, for connecting said negative pressure source and interfacing with oral cavity, and a negative pressure control unit, coupled to said physiological status extraction unit and said negative pressure source, for automatically controlling said negative pressure source based on said physiological status provided from said physiological status extraction unit.

Another exemplary embodiment provides a method applied in an oral appliance, for automatic controlling negative pressure supplied to a user's oral cavity. The method comprises: sensing a physiological signal from the user and outputting the sensed physiological signal; extracting a physiological status based on said sensed physiological signal; and automatically controlling the negative pressure provided to the user's oral cavity based on said physiological status.

Still yet another exemplary embodiment provides a method applied in an oral appliance, for automatic controlling a negative pressure supplied to a user's oral cavity, the method comprising: automatically controlling the negative pressure provided to the user's oral cavity based on time interval.

BRIEF DESCRIPTION OF THE DRAWINGS

It is to be understood that both the foregoing general description and the following detailed description are exemplary and explanatory only and are not restrictive of the disclosed embodiments, as claimed.

DETAILED DESCRIPTION OF EXEMPLARY EMBODIMENT OF THE INVENTION

Figure 1:
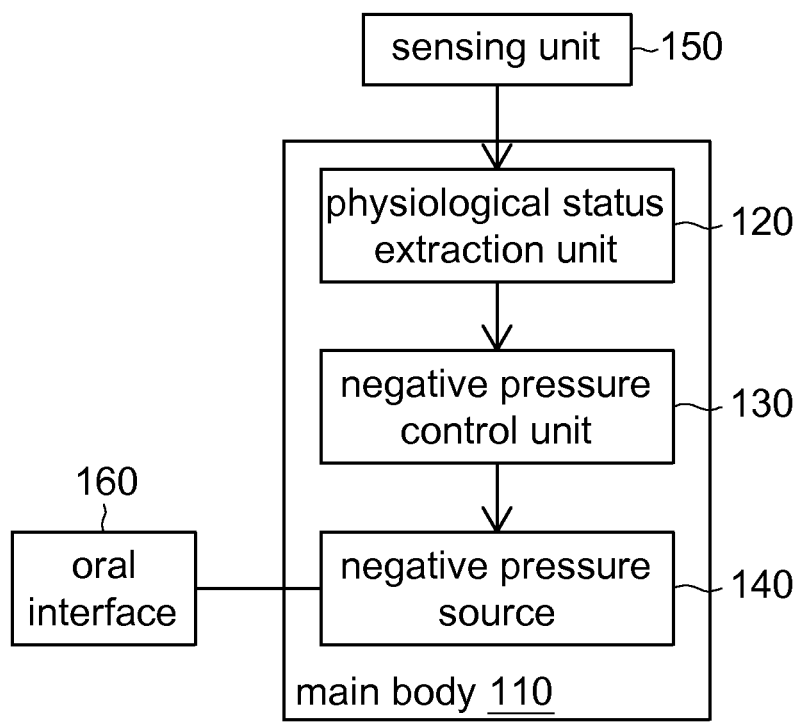
FIG. 1 shows a block diagram for an oral appliance with negative pressure for enhancing upper airway stability, according to an exemplary embodiment.

Reference will now be made in detail to the present exemplary embodiments, examples of which are illustrated in the accompanying drawings. Wherever possible, the same reference numbers are used in the drawings and the description to refer to the same or like parts.

FIG. 1 shows a block diagram for an oral appliance with negative pressure for enhancing upper airway stability, according to an exemplary embodiment. As shown in FIG. 1, the oral appliance 100 at least includes a main body 110, a sensing unit 150 and an oral interface 160. The main body 110 includes a physiological status extraction unit 120, a negative pressure control unit 130 and a negative pressure source 140.

The sensing unit 150 senses physiological signals feedback from a user and outputs the sensed physiological signals to the physiological status extraction unit 120. The sensing unit 150 includes at least one of the following sensors: position sensor, accelerator, gravity sensor, tilt sensor, motion sensor, electrodes, microphone, piezo-transducer, pressure sensor, oximeter, $CO_2$ sensor, thermistor, hotwire, flow sensor, respiratory inductive plethysmograph (RIP), strain gauge, impedance pneumograph, etc.

The physiological status extraction unit 120 extracts physiological status based on the signals from the sensing unit 150. The physiological status includes for example, body posture, sleep/wake status, Rapid Eye Movement (REM) period, muscle relaxation period, snore, oxygen ($O_2$) desaturation, $CO_2$ concentration in airway, breath event, heart rate variability, oral suction intent, open mouth intent etc.

The negative pressure control unit 130 controls the operation of the negative pressure source 140 based on the physiological status provided from the physiological status extraction unit 120. The control of the negative pressure control unit for example includes auto pressure on, auto pressure off, pressure increase, pressure decrease, intermittent, on-demand, auto relaxation, auto titration, auto pressure adjustment etc. Intermittent refers to that the negative pressure is turned on and turned off periodically, instead of being continuously on. On-demand control refers to that the negative pressure is activated when a patient is having or prone to have a sleep-breathing disorder event, instead of being continuously supplied. Auto relaxation refers to that the negative pressure is automatically decreased to a lower value for certain period of time, instead of being continuously at the fixed higher value of pressure setting. Auto titration control refers to that the oral appliance 100 will provide different negative pressure settings to a patient's oral cavity during a titrating period of time; and the optimized pressure setting with the least breathing disorder events corresponding to a patient's patterns of a plurality of breaths is automatically determined for the treatment of a patient's obstructive sleep apnea during the sleep.

The negative pressure source 140 supplies negative pressure in oral cavity. The negative pressure source 140 is controlled by the negative pressure control unit 130. The negative pressure supplied in oral cavity is for preventing airway occlusion during sleep, minimizing sleep apnea and snoring, by pulling the tongue and soft palate away from the posterior laryngeal wall, opening the airway through the nasal passage to facilitate natural breathing.

The oral interface 160 is for connecting the negative pressure supplied by the negative pressure source 140 when inserting in or interfacing with oral cavity.

The oral appliance according to the embodiment of the invention has several usage examples. In the following examples, the operating flows of different embodiments may be performed periodically.

EXAMPLE #1

Body Posture Detection

Figure 2A:
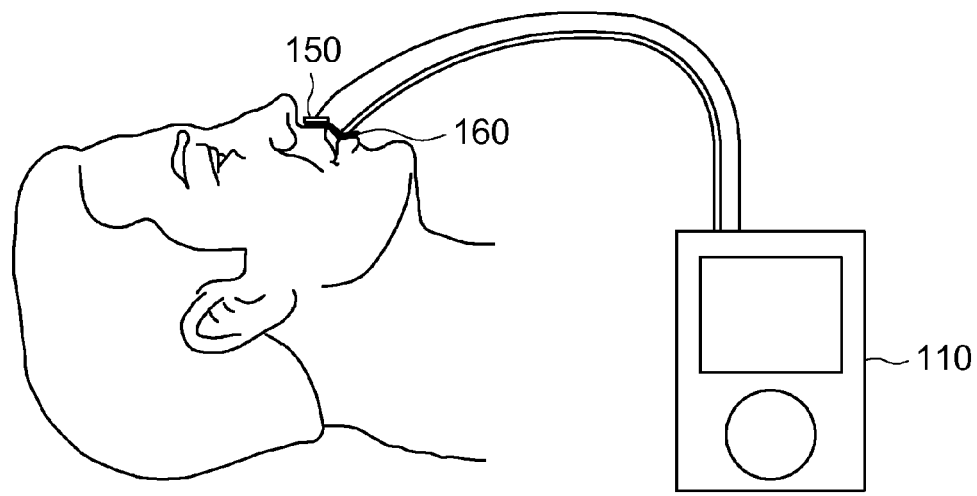
FIGS. 2A and 2B show an application diagram and a flow chart in an example #1 of the embodiment to control the negative pressure according to user body posture.
Figure 2B:
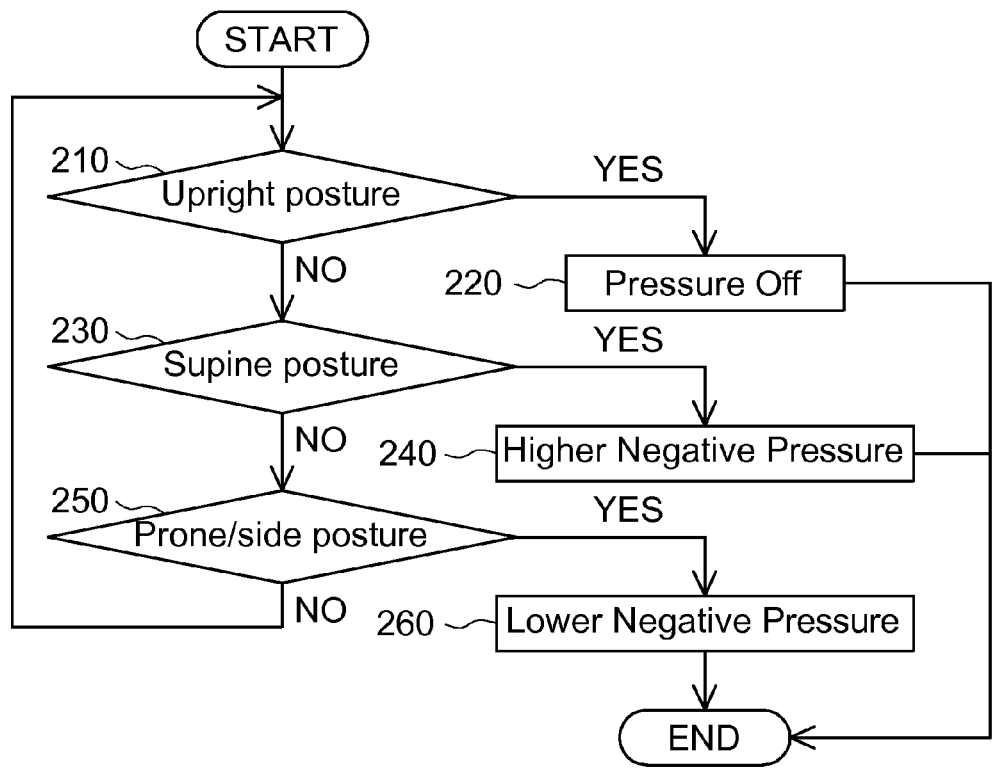

FIGS. 2A and 2B show an application diagram and a flow chart in an example #1 of the embodiment to control the negative pressure according to user body posture. In example #1, the sensing unit 150 may include at least one of a position sensor, an accelerator, a gravity sensor and a tilt sensor, etc.

Based on the sensing result of the sensing unit 150, the physiological status extraction unit 120 determines the body posture being upright posture, supine posture or prone/side posture. Now please refer to FIG. 2B, If the body posture is detected as upright posture (step 210), then the negative pressure control unit 130 turns off the negative pressure source 140 (step 220). If the body posture is detected as supine posture (step 230), which means patient is more likely to have OSA, hypopnea or UARS, then the negative pressure control unit 130 automatically controls the negative pressure (step 240), for example to increase the negative pressure to a higher value. If the negative pressure source 140 was turned off, then in step 240, the negative pressure control unit 130 automatically turns on the negative pressure source 140. If the body posture is detected as prone or side posture (step 250), which means OSA, hypopnea or UARS would be less likely occurred, then the negative pressure control unit 130 automatically controls the negative pressure, for example to decrease the negative pressure to a lower value. If the negative pressure source 140 was turned off, then in step 260, the negative pressure control unit 130 automatically turns on the negative pressure source 140. Further, in steps 240 or 260, the negative pressure is increased or decreased by predetermined values.

In example #1, the supplied negative pressure is adjusted based on body posture. When the body posture is upright posture, which means user does not lie down and OSA, hypopnea or UARS is less likely to occur, then the negative pressure source 140 is turned off, to reduce the power consumption of the oral appliance 100. If the body posture is supine, prone or side posture, which means the user may lie down and OSA, hypopnea or UARS is more likely to occur, then the negative pressure source 140 is on and controlled to generate negative pressure in user's oral cavity and to improve the patency of user's upper airway.

EXAMPLE #2

Sleep/Wake Detection

Figure 3A:
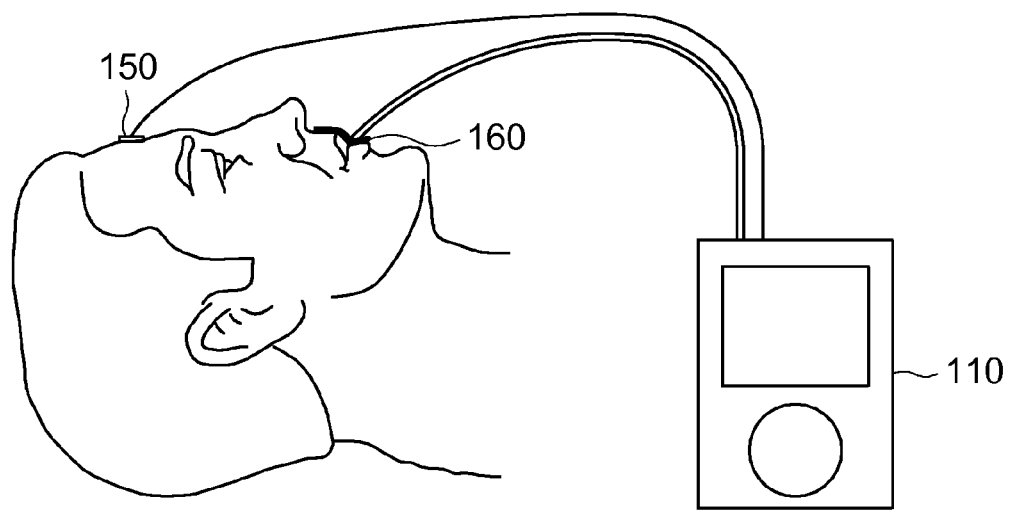
FIGS. 3A and 3B show an application diagram and a flow chart in an example #2 of the embodiment to control the negative pressure according to whether a user is asleep or awake.
Figure 3B:
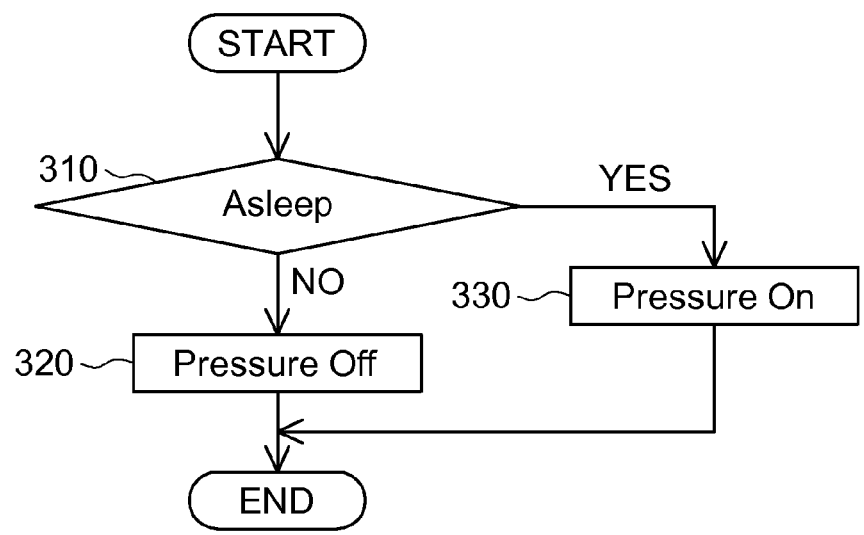

FIGS. 3A and 3B show an application diagram and a flow chart in an example #2 of the embodiment to control the negative pressure according to whether user is asleep or awake. In example #2, the sensing unit 150 may include at least one of an accelerator, a motion sensor or electrodes. If the sensing unit 150 is an accelerator or a motion sensor, the sensing unit 150 senses movement statuses of a user to determine whether the user is asleep or awake with less precise sleep-wakes staging. On the other hand, if the sensing unit 150 is electroencephalogram (EEG) electrodes, the sensing unit 150 senses brain waves (for example, α waves) of user to determine whether user is asleep or awake with more precise sleep-wakes staging.

Based on the sensing result of the sensing unit 150, the physiological status extraction unit 120 determines the user is asleep or awake. Now please refer to FIG. 3B, if user is awake (step 310), then the negative pressure control unit 130 automatically controls the negative pressure (step 320), for example, to turn off the negative pressure source 140. If user is asleep (step 310), then the negative pressure control unit 130 automatically controls the negative pressure (step 330), for example, to turn on the negative pressure source 140.

In example #2 the supplied negative pressure is adjusted based on whether user is asleep or awake. When user is awake, then the negative pressure source 140 is turned off, for reducing power consumption of the oral appliance 100. If user is asleep, then the negative pressure source 140 is powered on for providing negative pressure in oral cavity to improve the patency of user upper airway.

EXAMPLE #3

Rapid Eye Movement Detection

Figure 4A:
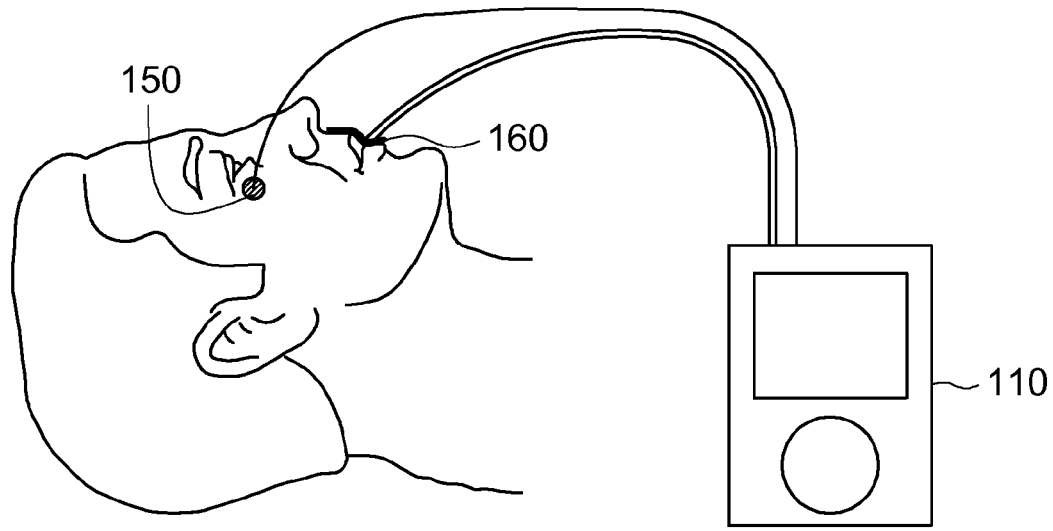
FIGS. 4A and 4B show an application diagram and a flow chart in an example #3 of the embodiment to control the negative pressure according to whether a user is in REM (Rapid Eye Movement) period.
Figure 4B:
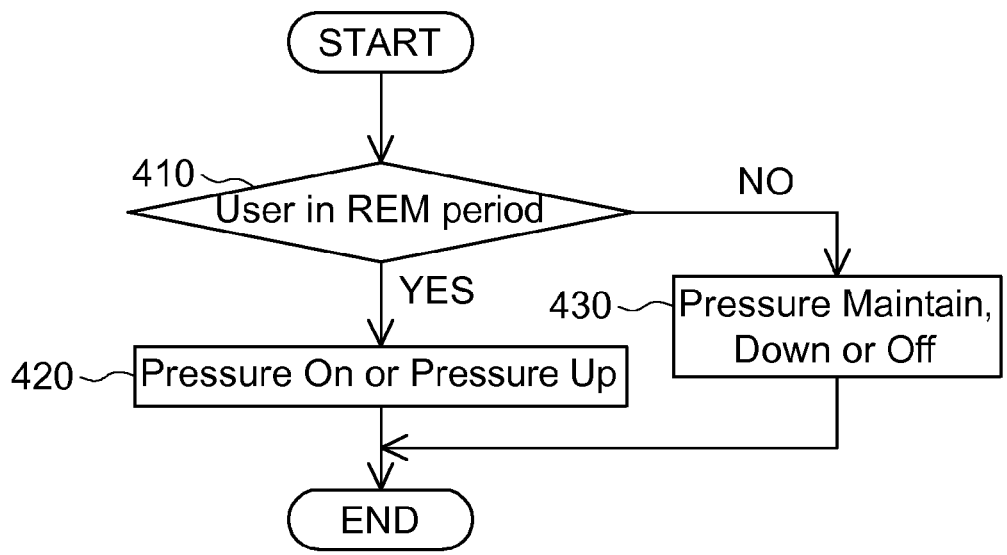

FIGS. 4A and 4B show an application diagram and a flow chart in an example #3 of the embodiment to control the negative pressure according to whether user is in REM (Rapid Eye Movement) period. In example #3, the sensing unit 150 may be Electrooculography (EOG) electrodes or Electromyography (EMG) electrodes, for sensing whether a user is in REM period. Snore, UARS or OSA is mostly occurred during REM period; and therefore, in example #3, if a user is detected to be in REM period, then the negative pressure is automatically controlled.

Based on the sensing result of the sensing unit 150, the physiological status extraction unit 120 determines whether a user is in REM period. Now please refer to FIG. 4B, if a user is in REM period (step 410), then the negative pressure control unit 130 automatically controls the negative pressure (step 420), for example to turn on the negative pressure source 140 or automatically increase the negative pressure by predefined values. If a user is not in REM period (step 410), then the negative pressure control unit 130 automatically controls the negative pressure (step 430), for example to maintain the negative pressure, automatically decrease the negative pressure, or eventually turn off the negative pressure. Further, in step 430, the negative pressure may be decreased by predetermined values.

In example #3 the supplied negative pressure is adjusted based on whether a user is in REM period. If a user is not in REM period, which means Snore, UARS or OSA may not occur, then the negative pressure is decreased or turned off, for reducing power consumption of the oral appliance 100. If a user is in REM period, then the negative pressure source 140 is powered on or the negative pressure is increased, for providing negative pressure in oral cavity to improve the patency of upper airway.

EXAMPLE #4

Muscle Relaxation Detection

Figure 5A:
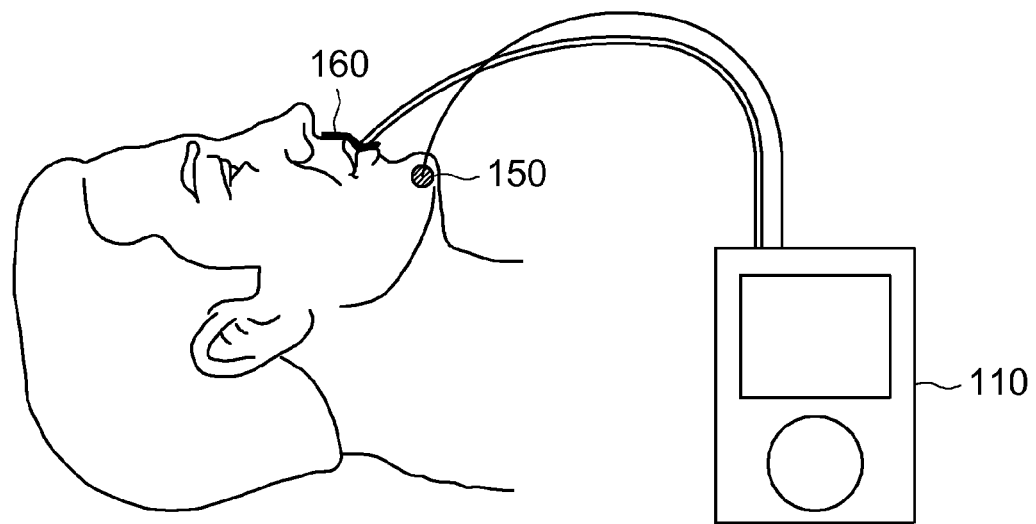
FIGS. 5A and 5B show an application diagram and a flow chart in an example #4 of the embodiment to control the negative pressure according to whether a user is in muscle relaxation period.
Figure 5B:
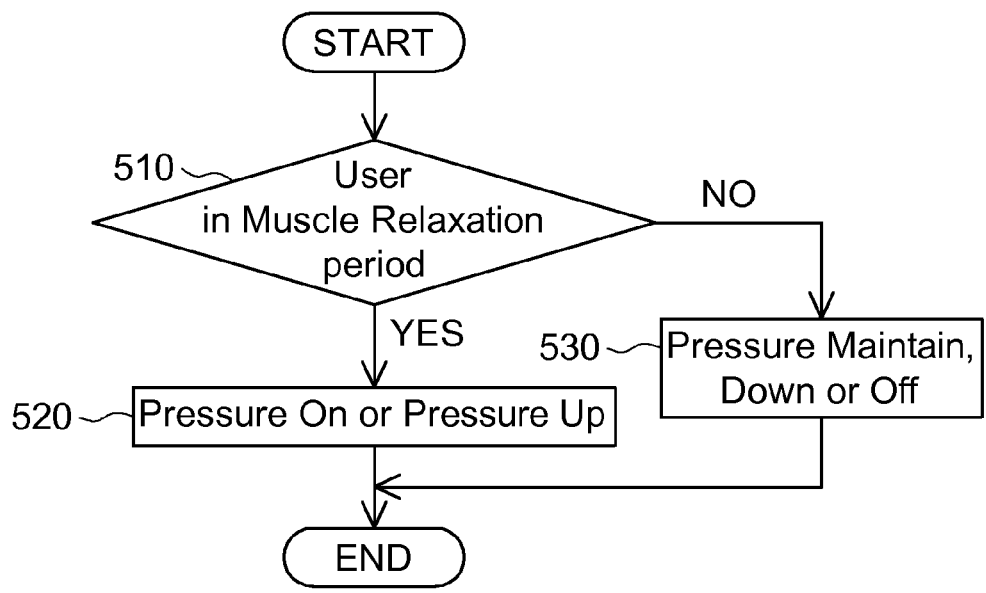

FIGS. 5A and 5B show an application diagram and a flow chart in an example #4 of the embodiment to control the negative pressure according to whether a user is in muscle relaxation period. In example #4, the sensing unit 150 may be Electrooculography (EOG) electrodes or Electromyography (EMG) electrodes, for sensing whether a user is in muscle relaxation period. Snore, UARS or OSA tends to occur during muscle relaxation period; and therefore, in example #4, if a user is detected to be in muscle relaxation period, then the negative pressure is automatically controlled.

Based on the sensing result of the sensing unit 150, the physiological status extraction unit 120 determines whether a user is in muscle relaxation period. Now please refer to FIG. 5B, if a user is in muscle relaxation period (step 510), then the negative pressure control unit 130 automatically controls the negative pressure (step 520), for example to turn on the negative pressure source 140 or automatically increase the negative pressure. If a user is not in muscle relaxation period (step 510), then the negative pressure control unit 130 automatically controls the negative pressure (step 530), for example to maintain the negative pressure, automatically decrease the negative pressure, or eventually turn off the negative pressure. Further, in step 520 or 530, the negative pressure may be increased or decreased by predetermined values.

In example #4 the supplied negative pressure is adjusted based on whether a user is in muscle relaxation period. If a user is not in muscle relaxation period, which means snore, UARS or OSA may not occur, then the negative pressure is decreased, for reducing power consumption of the oral appliance 100. If a user is in muscle relaxation period, then the negative pressure source 140 is powered on or the negative pressure is increased, for providing negative pressure in oral cavity to improve the patency of upper airway.

EXAMPLE #5

Snore Sound Detection

Figure 6A:
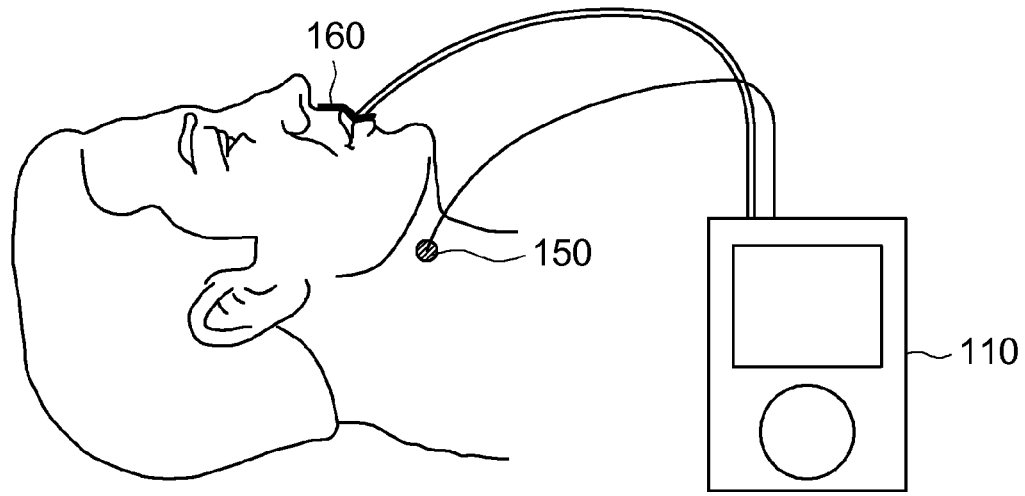
FIGS. 6A and 6B show an application diagram and a flow chart in an example #5 of the embodiment to control the negative pressure according to the detection of a snore sound.
Figure 6B:
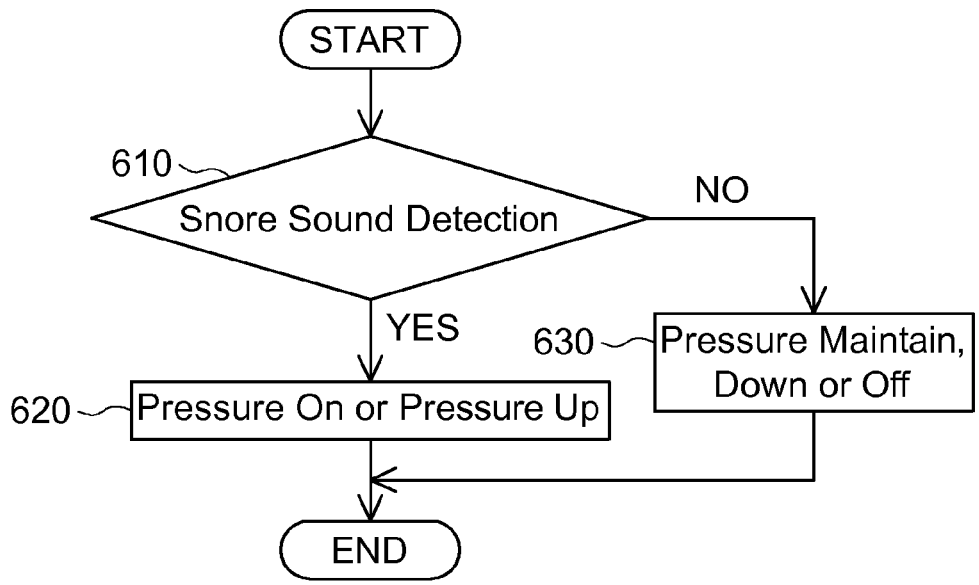

FIGS. 6A and 6B show an application diagram and a flow chart in an example #5 of the embodiment to control the negative pressure according to the detection of snore sound. In example #5, the sensing unit 150 may be a microphone or a piezo transducer, for sensing snore sound. UARS or OSA tends to occur when a user is snoring; and therefore, in example #5, if snore sound is detected, then the negative pressure is automatically controlled.

Based on the sensing result of the sensing unit 150, the physiological status extraction unit 120 determines the existence of snore sound. Now please refer to FIG. 6B, if snore sound is detected (step 610), then the negative pressure control unit 130 automatically controls the negative pressure (step 620), for example to turn on the negative pressure source 140 or automatically increase the negative pressure. If snore sound is not detected (step 610), then the negative pressure control unit 130 automatically controls the negative pressure (step 630), for example to maintain the negative pressure, automatically decrease the negative pressure, or turn off the negative pressure. Further, in step 620 or 630, the negative pressure may be increased or decreased by predetermined values.

In example #5, the supplied negative pressure is adjusted based on the detection of a snore sound. If a snore sound is not detected, which means UARS or OSA may not occur, then the negative pressure is turned off or decreased, for reducing power consumption. If snore sound is detected, then the negative pressure source 140 is powered on or the negative pressure is increased, for providing negative pressure in oral cavity to improve the patency of upper airway.

EXAMPLE #6

Airway Pressure Oscillation Detection

Figure 7A:
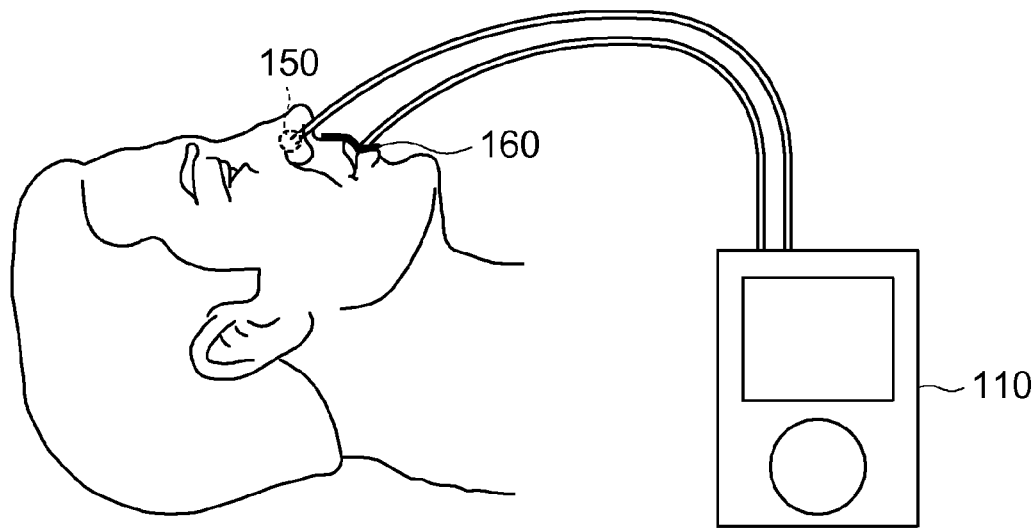
FIGS. 7A and 7B show an application diagram and a flow chart in an example #6 of the embodiment to control the negative pressure according to airway pressure oscillation caused by snoring.
Figure 7B:
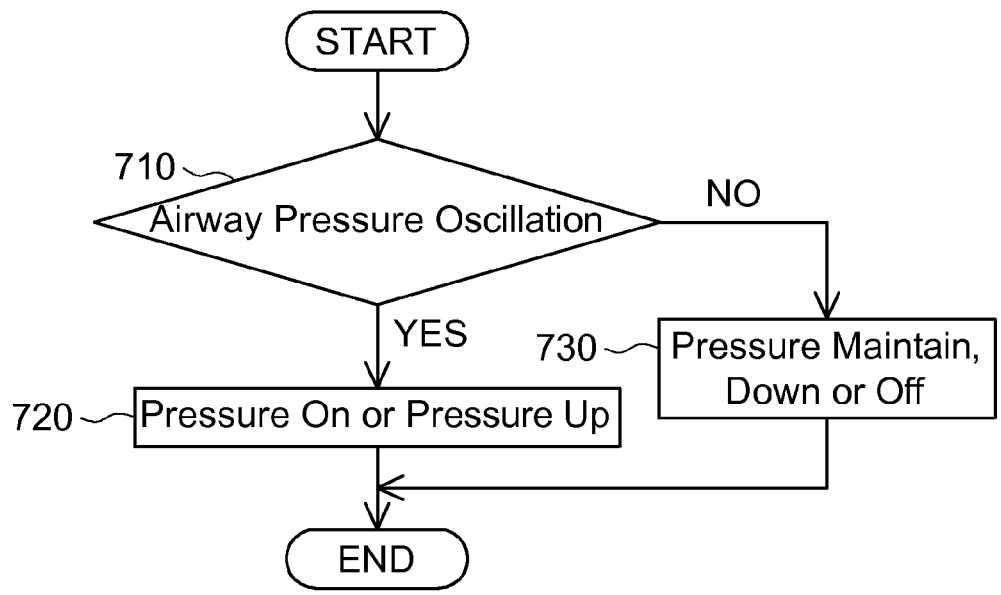

FIGS. 7A and 7B show an application diagram and a flow chart in an example #6 of the embodiment to control the negative pressure according to airway pressure oscillation (at higher frequencies than normal breathing) due to snore. In example #6, the sensing unit 150 may be a pressure sensor or a cannula connected to a pressure sensor, for sensing airway pressure and its oscillation. Snore can be identified by airway pressure oscillation. If snore is identified, which means UARS or OSA tends to occur, and therefore, in example #6, if airway pressure is oscillated, then the negative pressure is automatically controlled.

Based on the sensing result of the sensing unit 150, the physiological status extraction unit 120 determines the oscillation of airway pressure. Now please refer to FIG. 7B, if airway pressure is oscillated (step 710), then the negative pressure control unit 130 automatically controls the negative pressure (step 720), for example to turn on the negative pressure source 140 or automatically increase the negative pressure. If airway pressure is not oscillated (step 710), then the negative pressure control unit 130 automatically controls the negative pressure (step 730), for example to maintain the negative pressure, automatically decrease the negative pressure, or turn off the negative pressure. Further, in step 720 or 730, the negative pressure may be increased or decreased by predetermined values.

In example #6, the supplied negative pressure is adjusted based on the oscillation of airway pressure. If airway pressure is not oscillated, which means Snore is not present, then the negative pressure is turned off or decreased, for reducing power consumption. If airway pressure is oscillated, then the negative pressure source 140 is powered on or the negative pressure is increased, for providing negative pressure in oral cavity to improve the patency of upper airway.

EXAMPLE #7

$O_2$ Desaturation Detection

Figure 8A:
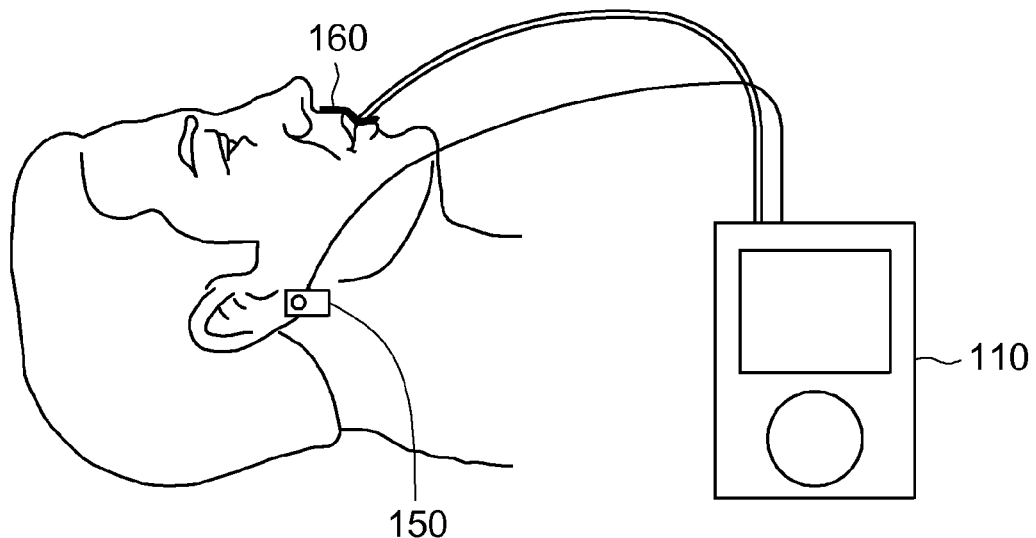
FIGS. 8A and 8B show an application diagram and a flow chart in an example #7 of the embodiment to control the negative pressure according to $O_2$ desaturation detection.
Figure 8B:
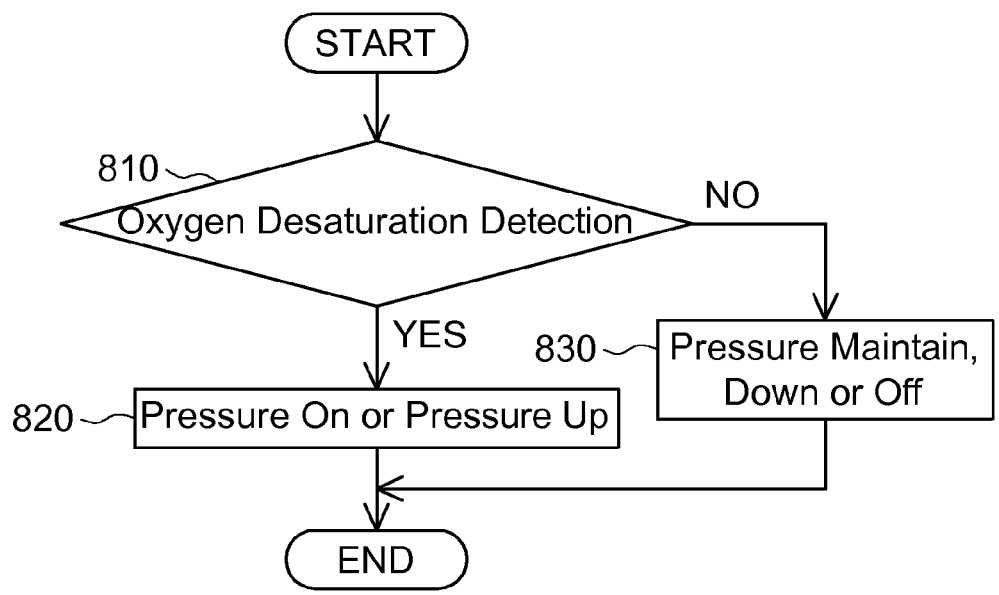

FIGS. 8A and 8B show an application diagram and a flow chart in an example #7 of the embodiment to control the negative pressure according to $O_2$ desaturation detection. In example #7, the sensing unit 150 may include an oximeter, for sensing $O_2$ concentration in blood vessels. UARS or OSA causes decrease of $O_2$ concentration in blood vessels; and therefore, in example #7, if $O_2$ concentration in blood vessels is decreased, then the negative pressure is automatically controlled.

Based on the sensing result of the sensing unit 150, the physiological status extraction unit 120 determines the $O_2$ concentration in blood vessels. Now please refer to FIG. 8B, if $O_2$ concentration in blood vessels is decreased (step 810), then the negative pressure control unit 130 automatically controls the negative pressure (step 820), for example to turn on the negative pressure source 140 or automatically increase the negative pressure. If $O_2$ concentration in blood vessels is kept (step 810), then the negative pressure control unit 130 automatically controls the negative pressure (step 830), for example to maintain the negative pressure, automatically decrease the negative pressure, or turn off the negative pressure. Further, in step 820 or 830, the negative pressure may be increased or decreased by predetermined values.

In example #7, the supplied negative pressure is adjusted based on whether $O_2$ concentration in blood vessels is decreased. If $O_2$ concentration in blood vessels is not decreased, which means UARS or OSA may not occur, then the negative pressure is decreased or turned off, for reducing power consumption. If $O_2$ concentration in blood vessels is decreased, which means UARS or OSA may occur, then the negative pressure source 140 is powered on or the negative pressure is increased, for providing negative pressure in oral cavity to improve the patency of upper airway.

EXAMPLE #8

$CO_2$ Concentration Detection

Figure 9A:
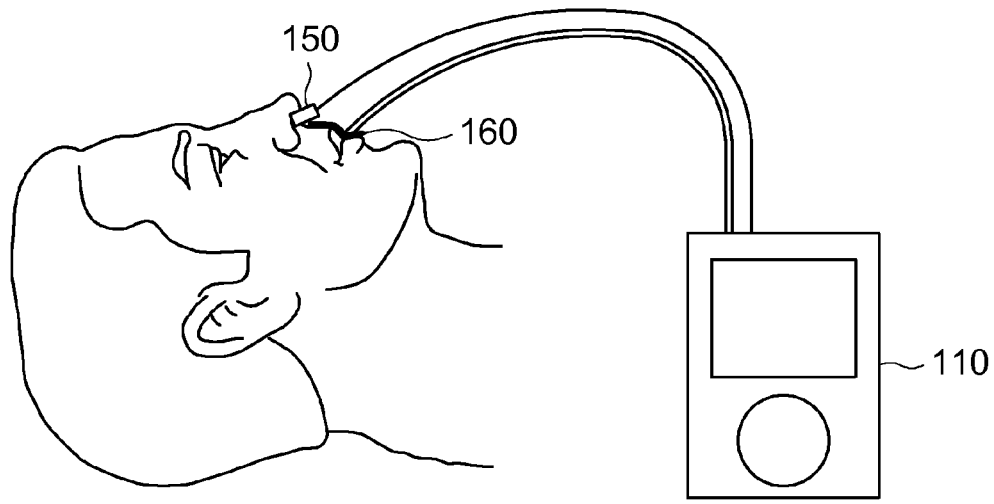
FIGS. 9A and 9B show an application diagram and a flow chart in an example #8 of the embodiment to control the negative pressure according to $CO_2$ concentration in airway.
Figure 9B:
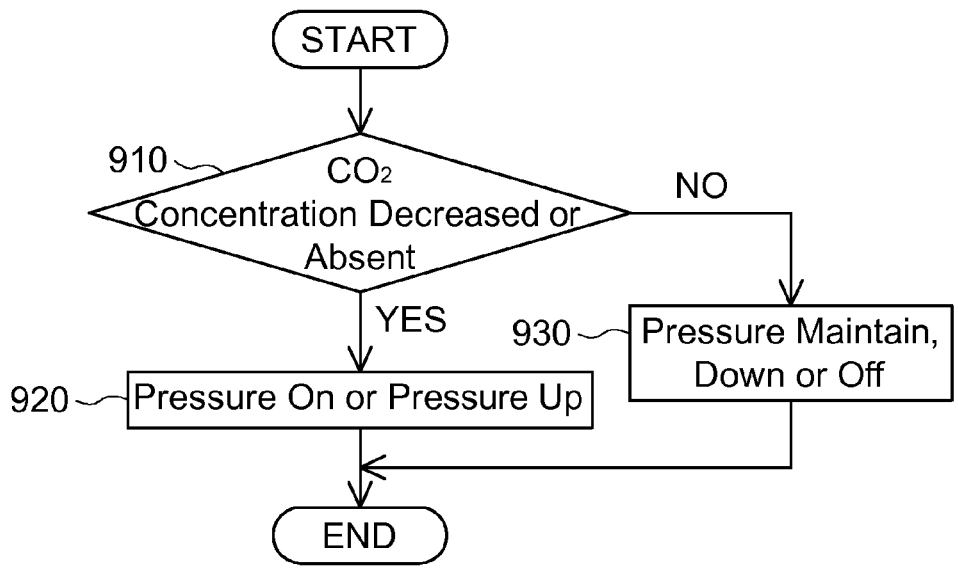

FIGS. 9A and 9B show an application diagram and a flow chart in an example #8 of the embodiment to control the negative pressure according to $CO_2$ concentration in airway. In example #8, the sensing unit 150 may include a $CO_2$ sensor, for sensing $CO_2$ concentration in airway. UARS or OSA causes low or absent end-tidal $CO_2$ concentration; and therefore, in example #8, if end-tidal $CO_2$ concentration in airway is decreased or absent, then the negative pressure is automatically controlled.

Based on the sensing result of the sensing unit 150, the physiological status extraction unit 120 determines the end-tidal $CO_2$ concentration in airway. Now please refer to FIG. 9B, if end-tidal $CO_2$ concentration in airway is decreased or absent (step 910), then the negative pressure control unit 130 automatically controls the negative pressure (step 820), for example to turn on the negative pressure source 140 or automatically increase the negative pressure. If end-tidal $CO_2$ concentration in airway is kept or not decreased (step 910), then the negative pressure control unit 130 automatically controls the negative pressure (step 930), for example to maintain the negative pressure, automatically decrease the negative pressure, or turn off the negative pressure. Further, in step 920 or 930, the negative pressure may be increased or decreased by predetermined values.

In example #8, the supplied negative pressure is adjusted based on whether end-tidal $CO_2$ concentration in airway is decreased or absent. If $CO_2$ concentration in airway is kept, which means UARS or OSA may not occur, then the negative pressure is decreased or turned off, for reducing power consumption. If $CO_2$ concentration in airway is decreased, which means Snore, UARS or OSA may occur, then the negative pressure source 140 is powered on or the negative pressure is increased, for providing negative pressure in oral cavity to improve the patency of upper airway.

EXAMPLE #9

Abnormal Breathing Detection

Figure 10A:
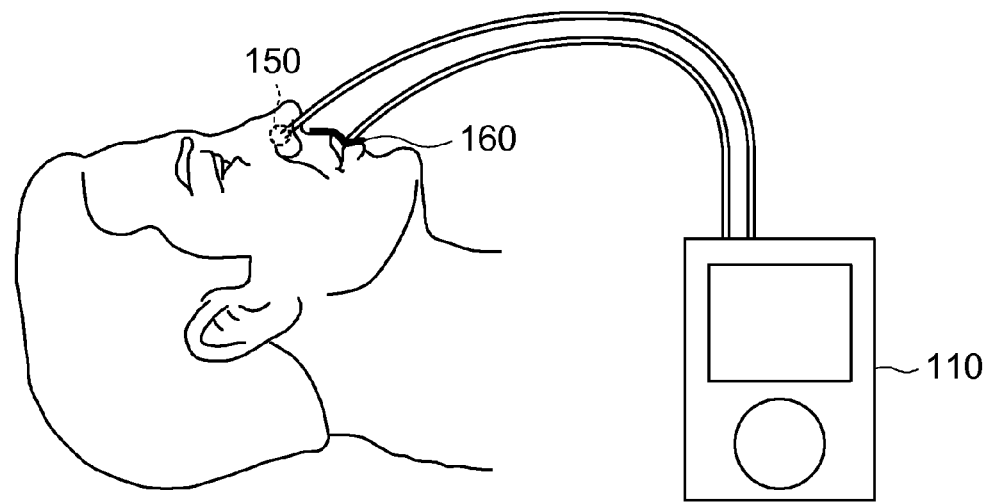
FIG. 10A-10C and FIG. 10D show application diagrams and a flow chart in an example #9 of the embodiment to control the negative pressure according to abnormal breathing detection.
Figure 10B:
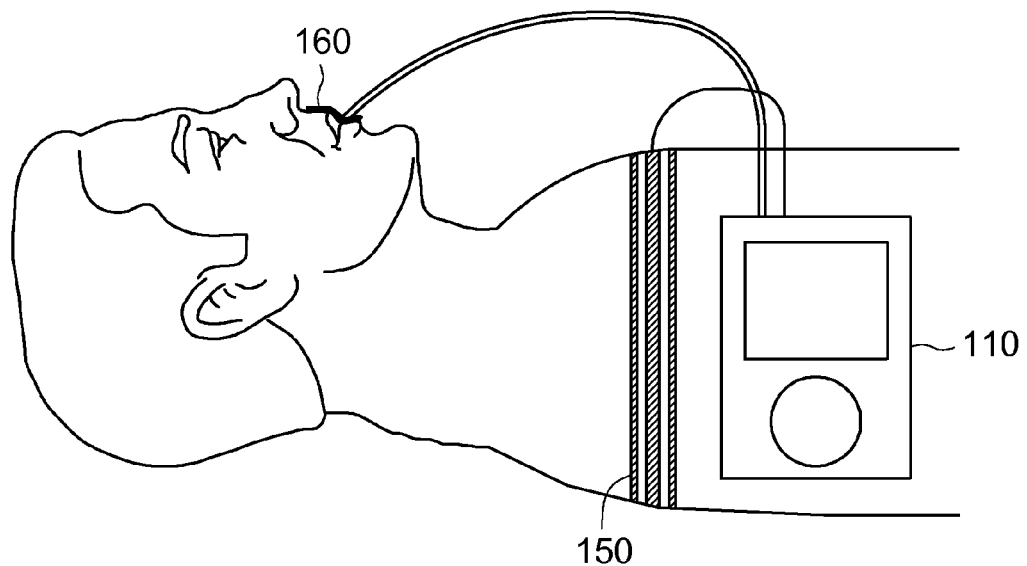
Figure 10C:
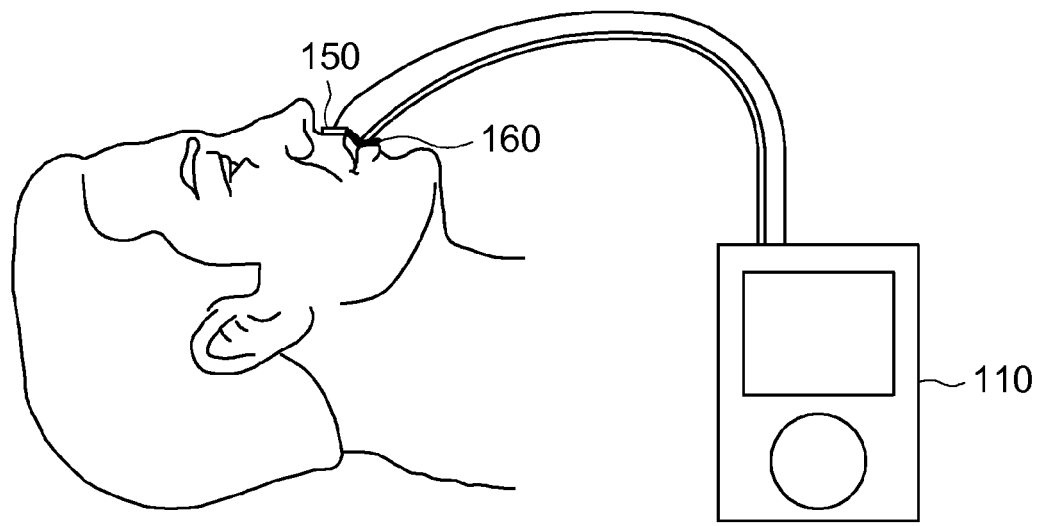

FIGS. 10A-10C and FIG. 10D show application diagrams and a flow chart in an example #9 of the embodiment to control the negative pressure according to abnormal breathing detection. The sensing unit 150 may be a pressure sensor or a cannula connected to a pressure sensor for sensing pressure variation in airway, as shown in FIG. 10A. The sensing unit 150 may be a respiratory inductive plethysmograph, a strain gauge or an impedance pneumograph for sensing abdominal breathing and/or thoracic breathing, as shown in FIG. 10B. The sensing unit 150 may be a thermistor air flow sensor or a hotwire sensor for sensing flow variation in airway, as shown in FIG. 10C.

Based on the sensing result of the sensing unit 150, the physiological status extraction unit 120 determines whether abnormal breathing event is presented. Snore, UARS or OSA causes abnormal breathing events. Therefore, in example #9, if an abnormal breathing event is detected, then the negative pressure is automatically controlled.

Figure 10D:
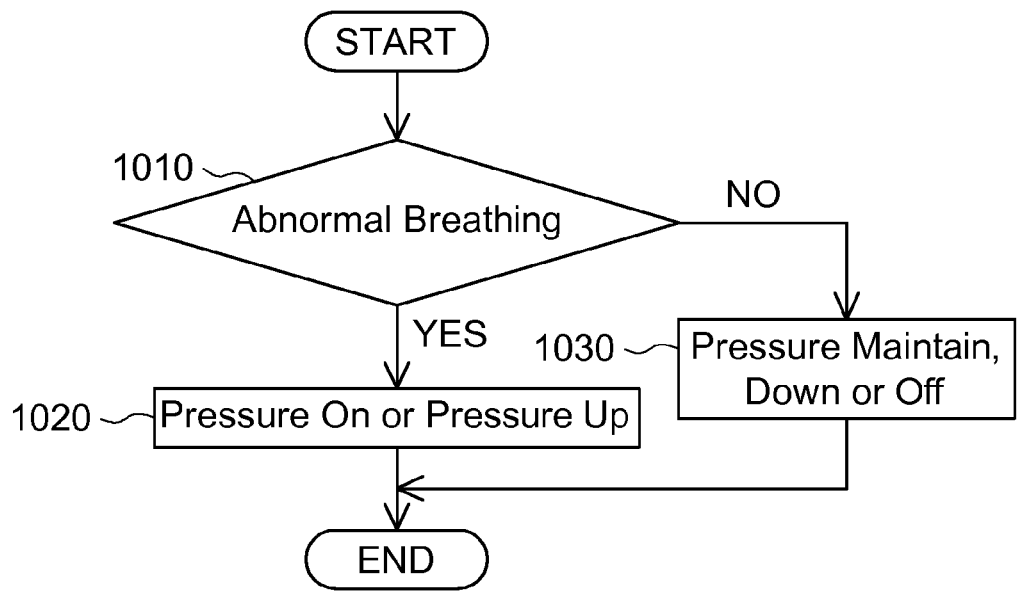

Now please refer to FIG. 10D, if an abnormal breathing event is detected (step 1010), then the negative pressure control unit 130 automatically controls the negative pressure (step 1020), for example to turn on the negative pressure source 140 or automatically increase the negative pressure. If an abnormal breathing event does not occur (step 1010), then the negative pressure control unit 130 automatically controls the negative pressure (step 1030), for example to maintain the negative pressure, automatically decrease the negative pressure, or turned off the negative pressure. Further, in step 1020 or 1030, the negative pressure may be increased or decreased by predetermined values.

In example #9, the supplied negative pressure is adjusted based on whether breath is abnormal. If not, which means snore, UARS or OSA may not occur, then the negative pressure is turned off or decreased, for reducing power consumption. If yes, which means snore, UARS or OSA may occur, then the negative pressure source 140 is powered on or the negative pressure is increased, for providing negative pressure in oral cavity to improve the patency of upper airway.

Still further, in the example #9, automatic negative pressure control may be performed based on breath phase. Based on the sensing result of the sensing unit 150 in FIG. 10A, 10B or 10C, the physiological status extraction unit 120 determines breath phase (exhalation or inhalation). In exhalation phase, the negative pressure is automatically decreased by the negative pressure control unit 130. On the other hand, in inhalation phase, the negative pressure is automatically increased by the negative pressure control unit 130.

The negative pressure control unit 130 provides different negative pressure to a patient's oral cavity during a titrating period of time; and the said physiological status extraction unit 120 determines an optimized pressure setting with least breathing disorder events corresponding to a patient's breaths patterns.

EXAMPLE #10

Heart Rate Variability (HRV) Detection

Figure 11A:
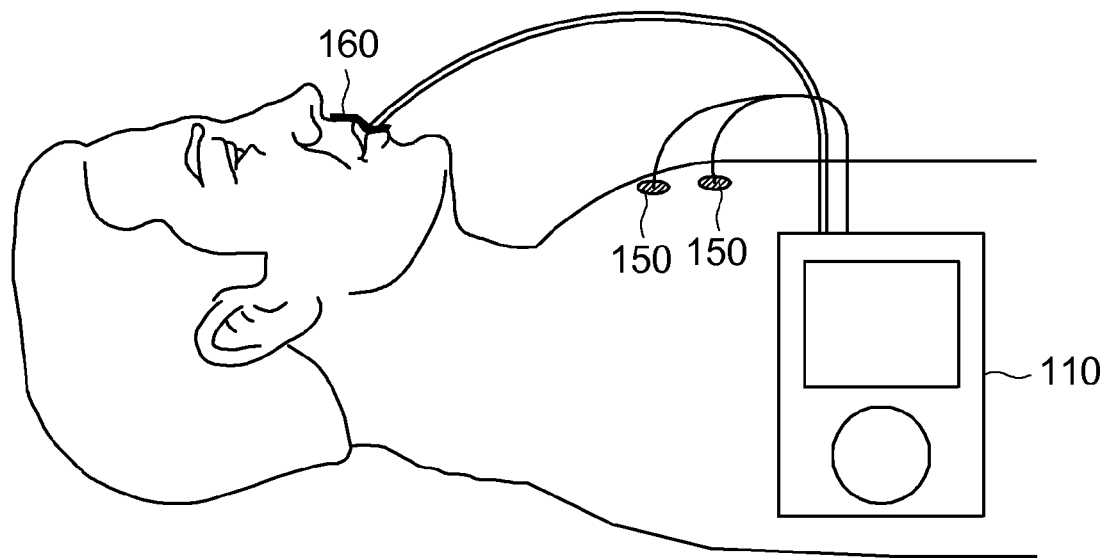
FIG. 11A-11B and FIG. 11C show application diagrams and a flow chart in an example #10 of the embodiment to control the negative pressure according to HRV detection.
Figure 11B:
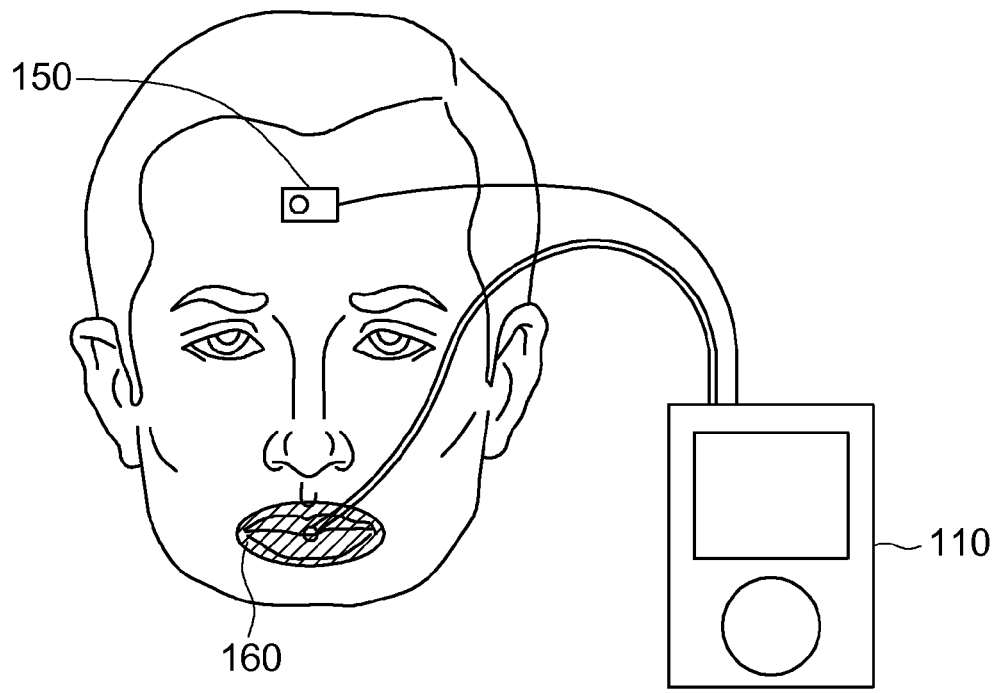
Figure 11C:
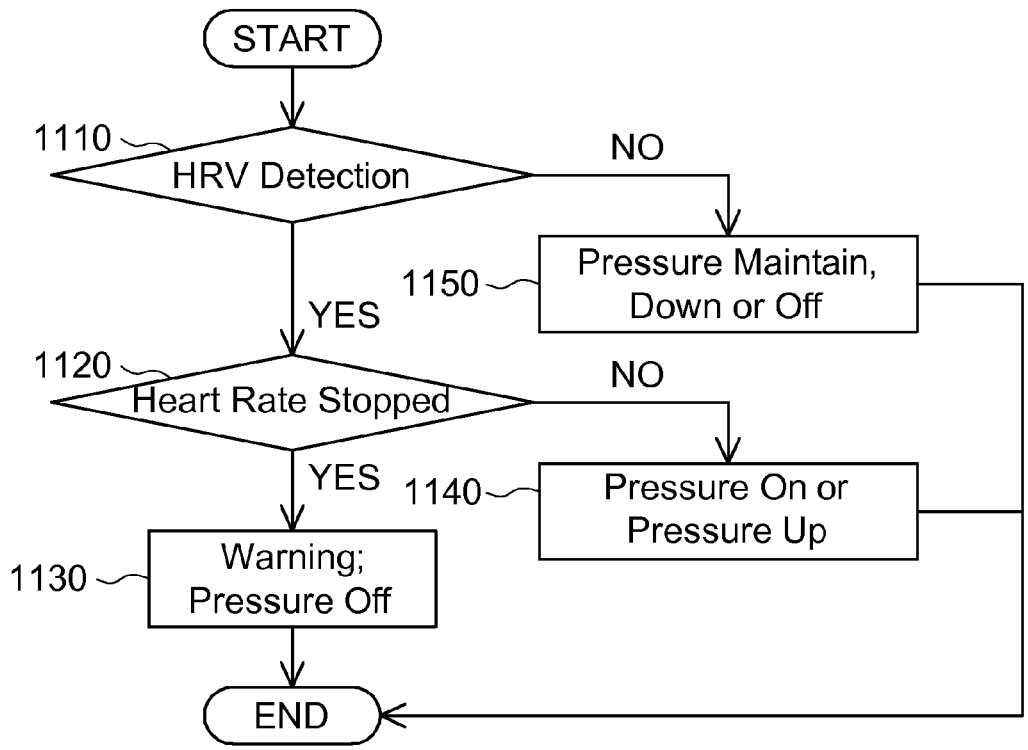

FIGS. 11A-11B and FIG. 11C show application diagrams and a flow chart in an example #10 of the embodiment to control the negative pressure according to HRV detection. In FIG. 11A, the sensing unit 150 may be Electro-Cardiogram (ECG) electrodes for sensing electrical activity of the heart. In FIG. 11 B, the sensing unit 150 may include a photoplethysmography (PPG) for sensing cardiac cycles.

Based on the sensing result of the sensing unit 150, the physiological status extraction unit 120 determines HRV or whether heart rate is abnormal or stopped. UARS or OSA is associated with high heart rate variability, wherein heart rate variability may be resulted from apnea. Therefore, in example #10, if high HRV is detected, then the negative pressure is automatically controlled.

Now please refer to FIG. 11C, if high HRV is detected (step 1110), then it is determined whether heart rate is abnormal or stopped (step 1120). If heart rate is abnormal or stopped, then a warning signal is generated and the negative pressure source 140 is automatically turned off by the negative pressure control unit 130. If HRV is detected and heart rate is not stopped, then the negative pressure control unit 130 automatically controls the negative pressure (step 1140), for example to turn on the negative pressure source 140 or automatically increase the negative pressure. If high HRV does not occur (step 1110), then the negative pressure control unit 130 automatically controls the negative pressure (step 1150), for example to maintain the negative pressure, automatically decrease the negative pressure, or turn off the negative pressure. Further, in step 1140 or 1150, the negative pressure may be increased or decreased by predetermined values.

In example #10, the supplied negative pressure is adjusted based on whether HRV is over a threshold. If not, which means UARS or OSA may not occur, then the negative pressure is turned off or decreased, for reducing power consumption. If yes, which means UARS or OSA may occur, then the negative pressure source 140 is powered on or the negative pressure is increased, for providing negative pressure in oral cavity to improve the patency of upper airway.

EXAMPLE #11

Oral Suction Intent Detection

Figure 12A:
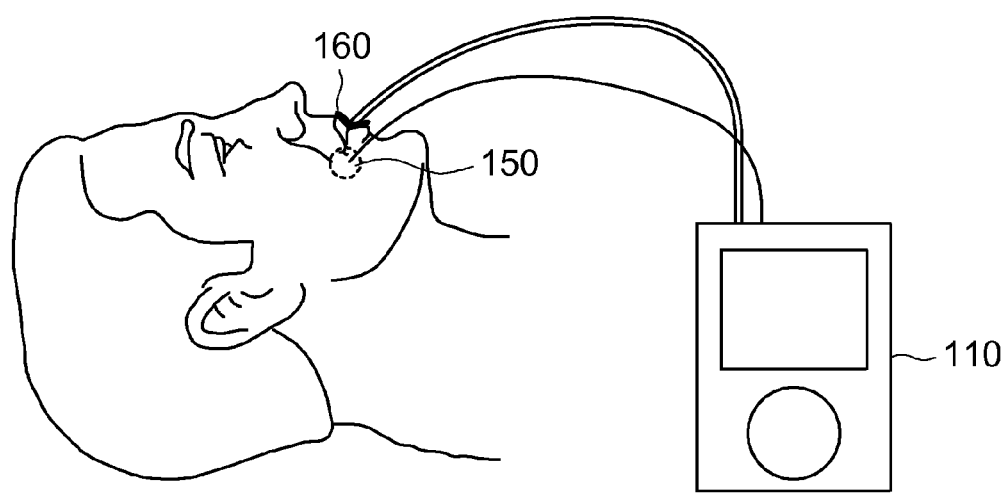
FIG. 12A and FIG. 12B show an application diagram and a flow chart in an example #11 of the embodiment to control the negative pressure according to oral suction intent detection.
Figure 12B:
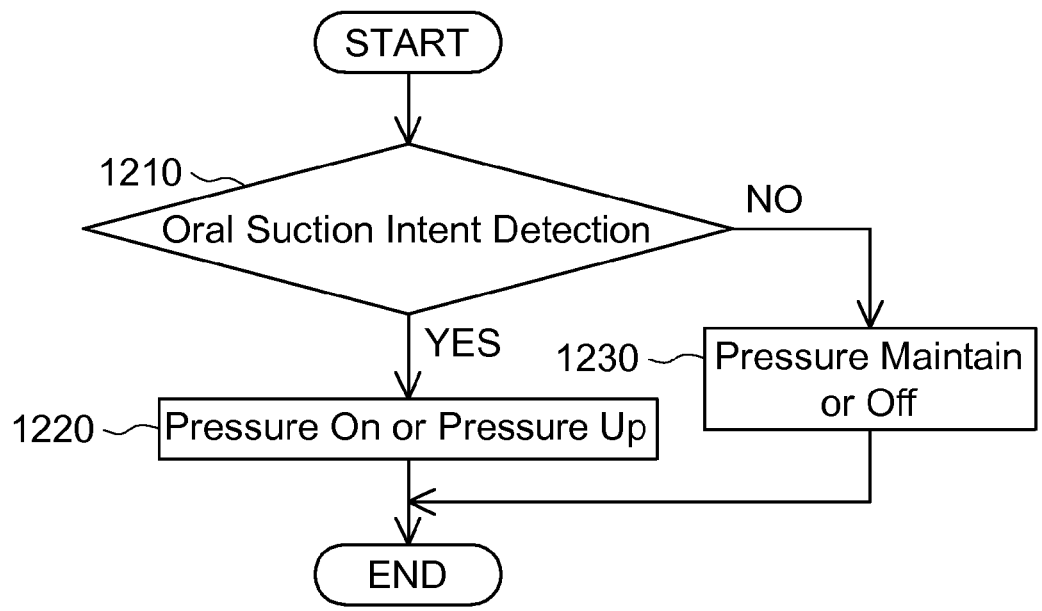

FIG. 12A and FIG. 12B show an application diagram and a flow chart in an example #11 of the embodiment to control the negative pressure according to oral suction intent detection. In FIG. 12A, the sensing unit 150 may be a pressure sensor or a cannula connected to a pressure sensor for sensing pressure in an oral cavity. Based on the sensing result of the sensing unit 150, the physiological status extraction unit 120 determines oral suction intent. Further, if the pressure in oral cavity is decreased, then the physiological status extraction unit 120 determines intent in oral suction, which represents user's intent to provide negative pressure to the oral cavity. Therefore, in example #11, if oral suction intent is detected, then the negative pressure is automatically controlled.

Now please refer to FIG. 12B, if oral suction intent is detected (step 1210), then the negative pressure control unit 130 automatically controls the negative pressure (step 1220), for example to turn on the negative pressure source 140 or automatically increase the negative pressure. If no oral suction intent is detected (step 1210), then the negative pressure control unit 130 automatically controls the negative pressure (step 1230), for example to automatically turn off the negative pressure source 140 or maintain the negative pressure. Further, in step 1220, the negative pressure may be increased by predetermined values.

In example #11, the negative pressure is adjusted based on oral suction intent. If no oral suction intent, which means a user has no intention to provide negative pressure to the oral cavity then the negative pressure is not turned on, for reducing power consumption. If oral suction intent is detected, which means a user has an intention to provide negative pressure to the oral cavity, then the negative pressure source 140 is powered on or the negative pressure is increased, for providing negative pressure in oral cavity to improve the patency of upper airway.

EXAMPLE #12

Open Mouth Intent Detection

Figure 13A:
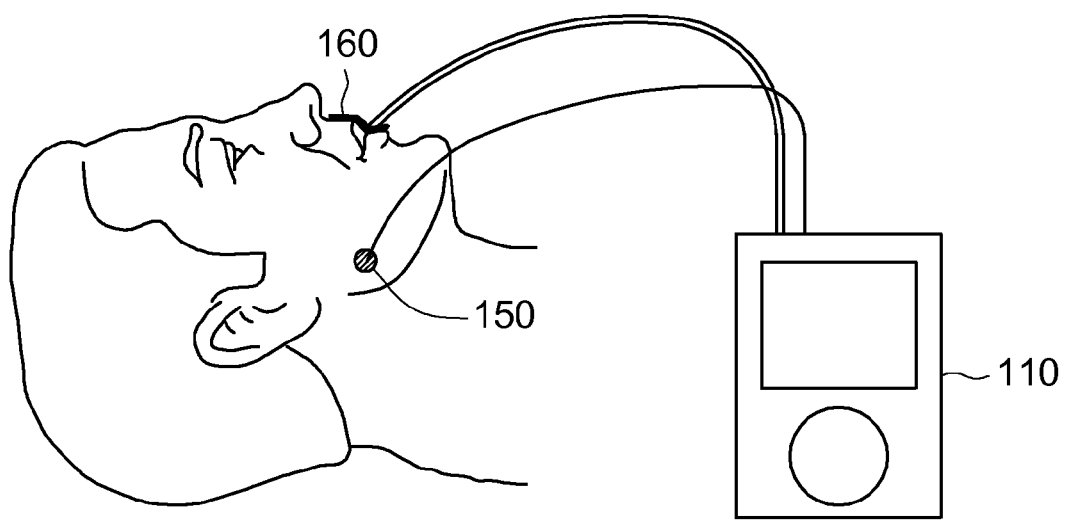
FIG. 13A and FIG. 13B show an application diagram and a flow chart in an example #12 of the embodiment to control the negative pressure according to open mouth detection.
Figure 13B:
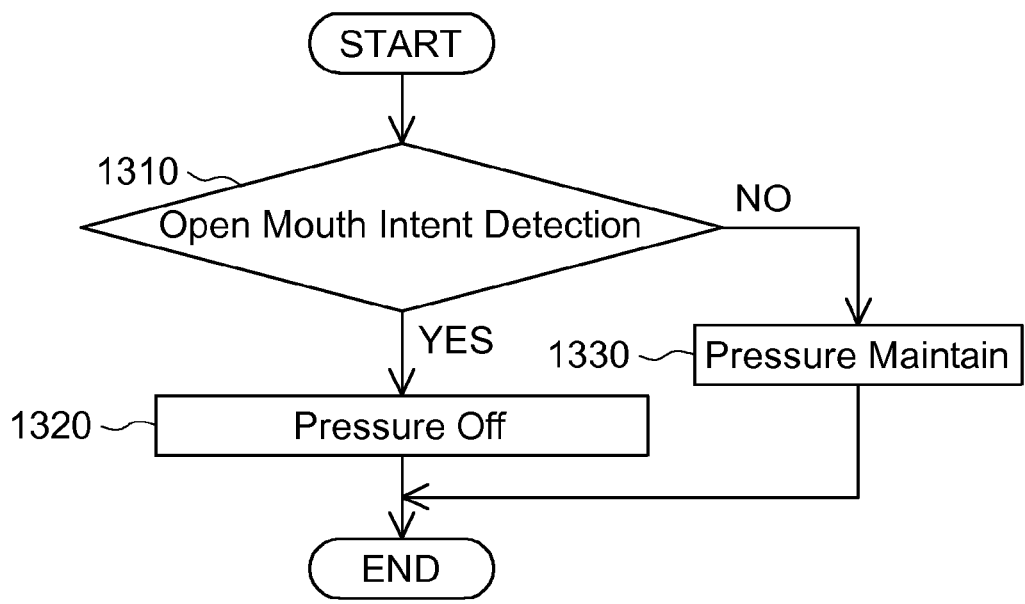

FIGS. 13A and 13B show an application diagram and a flow chart in an example #12 of the embodiment to control the negative pressure according to open mouth intent detection. In FIG. 13A, the sensing unit 150 may be electromyography electrodes for sensing electrical activity of muscles near mouth or jaw. Based on the sensing result of the sensing unit 150, the physiological status extraction unit 120 determines open mouth intent. Further, if open mouth intent is detected, which means a user have an intention to open mouth, providing negative pressure to the oral cavity is stopped. Therefore, in example #12, if open mouth intent is detected, then the negative pressure is automatically controlled.

Now please refer to FIG. 13B, if open mouth intent is detected (step 1310), then the negative pressure control unit 130 automatically controls the negative pressure (step 1320), for example to turn off the negative pressure source 140. If open mouth intent does not occur (step 1310), then the negative pressure control unit 130 automatically controls the negative pressure (step 1330), for example to maintain the negative pressure.

In example #12, the negative pressure is adjusted based on open mouth intent. If a user has an intention to open mouth, then the negative pressure is turned off, for reducing power consumption. If no open mouth intent is detected, then the negative pressure is maintained, for providing negative pressure in oral cavity to improve the patency of upper airway.

In the above examples, the flow chart is performed periodically. Further, anyone of the examples would be modified and combined with other example. For example, but not limited, the example #2 would be modified and combined with the example #1, so that, if the a user is detected as being in asleep, then the body posture of a user asleep would be detected as those in the example 1, for further controlling the negative pressure.

EXAMPLE #13

Automatic Negative Pressure Control

Figure 14:
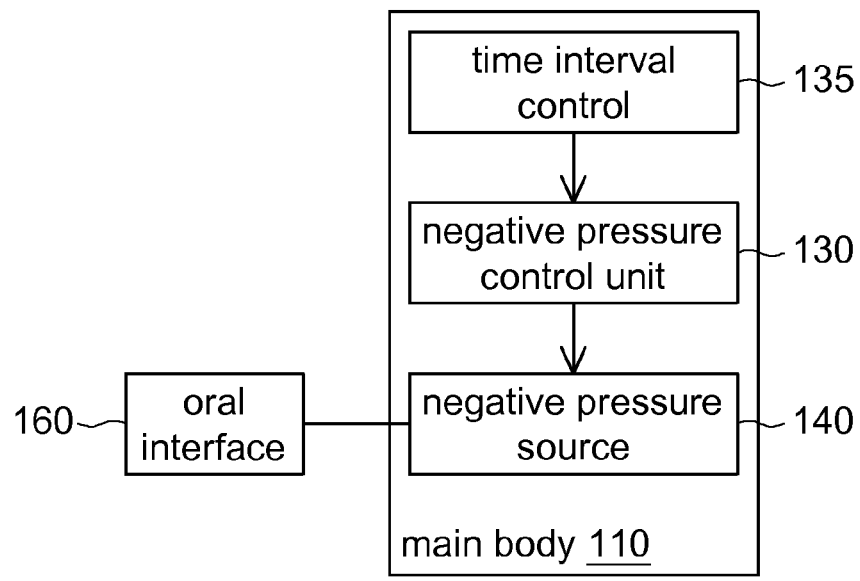
FIG. 14 shows a block diagram for an oral appliance with negative pressure for enhancing upper airway stability, in an example #13 of the exemplary embodiment to provide the time interval control.

Example #13 of the application provides an oral appliance with automatic negative pressure control and a method therefore. FIG. 14 shows a block diagram for the oral appliance with negative pressure for enhancing upper airway stability, in the example #13 of the exemplary embodiment to provide the time interval control. The oral appliance with automatic negative pressure control includes: a negative pressure source 140, for providing a negative pressure; an oral interface 160, for connecting said negative pressure source and interfacing with an oral cavity, and a negative pressure control unit 130 for controlling said negative pressure source based on a time interval control 135, such as auto on, auto pressure increase, intermittent, and auto relaxation. The negative pressure source 140, the negative pressure control unit 130 and the time interval control 135 are inside the main body 110. The negative pressure control unit 130 automatically turns the negative pressure on at a predetermined time interval after power on, under control of the time interval control. The negative pressure control unit 130 gradually increases the negative pressure to a predetermined value at a predetermined time interval after power on, under control of the time interval control. The negative pressure control unit 130 intermittently turns the negative pressure off and on at predetermined time periods, under control of the time interval control. The negative pressure control unit 130 periodically decreases the negative pressure to a low value for a predetermined time interval and then resuming to a high value, under control of the time interval control.

It will be appreciated by those skilled in the art that changes could be made to the disclosed embodiments described above without departing from the broad inventive concept thereof. It is understood, therefore, that the disclosed embodiments are not limited to the particular examples disclosed, but is intended to cover modifications within the spirit and scope of the disclosed embodiments as defined by the claims that follow.

What is claimed is:

1. A method applied in an oral appliance, for automatic controlling negative pressure supplied to a user's oral cavity, the oral appliance comprising: a sensing unit, a physiological status extraction unit, a negative pressure source, an oral interface, and a negative pressure control unit, and the method comprising:

sensing a physiological signal from a user and outputting the physiological signal by the sensing unit;

providing a negative pressure to an oral interface interfacing with the user's oral cavity by the negative pressure source; and extracting a physiological status based on the physiological signal by the physiological status extraction unit;

automatically controlling the negative pressure provided to the user's oral cavity based on the physiological status by the negative pressure control unit;

wherein the method further comprising:

determining a breath phase of the user in exhalation or in inhalation, and automatically turning on or increasing the negative pressure in inhalation phase, and automatically maintaining or turning off or decreasing the negative pressure in exhalation phase.

2. The method as in claim 1, wherein the physiological status is selected from the group consisting of body posture, sleep/wake status, rapid eye movement period, muscle relaxation period, snore sound, oxygen desaturation, $CO_2$ concentration, abnormal breathing event, breath phase, heart rate variability, oral suction intent and open mouth intent.

3. The method as in claim 1, wherein the step of sensing a physiological signal from the user and outputting the physiological signal includes:

sensing the physiological signal by a sensing unit which is selected from the group consisting of a body position sensor, an accelerator, a gravity sensor, a tilt sensor, a motion sensor, electrodes, a microphone, a piezo-transducer, a pressure sensor, an oximeter, a CO2 sensor, a thermistor, a hotwire, a flow sensor, a respiratory inductive plethysmograph, a strain gauge and an impedance pneumograph.

4. The method according to claim 1, wherein the step of automatically controlling the negative pressure is performed by selected from the group consisting of turning pressure on, turning pressure off, setting pressure high, setting pressure low, increasing pressure, decreasing pressure, intermittent, on-demand, auto relaxation, auto titration and maintaining pressure.

5. The method as in claim 1, further comprising:
determining the user's body position in upright, supine, prone or side posture.

6. The method as in claim 1, further comprising:
determining the user's sleep/wake status.

7. The method as in claim 1, further comprising:
determining the user in rapid eye movement period.

8. The method as in claim 1, further comprising:
determining the user in muscle relaxation period.

9. The method as in claim 1, further comprising:
determining if the user has snore sound.

10. The method as in claim 1, further comprising:
determining if the user has airway pressure oscillation.

11. The method as in claim 1, further comprising:
determining if the user has oxygen desaturation.

12. The method as in claim 1, further comprising:
determining if the user has lower or absent tidal-end CO2 concentration.

13. The method as in claim 1, further comprising:
determining if the user has abnormal breathing events.

14. The method as in claim 1, further comprising:
determining if the user has high heart rate variability.

15. The method as in claim 1, further comprising:
determining if the user has oral suction intent.

16. The method as in claim 1, further comprising:
determining if the user has open mouth intent.

17. The method as in claim 1, further comprising:
providing different negative pressure to the user's oral cavity during a titrating period of time; and
determining an optimized pressure setting with the least breathing disorder events corresponding to a plurality of breaths patterns of the user.

18. The method as in claim 17, wherein the negative pressure supplied is adjusted based on whether the user abnormal breathing events.

19. The method as in claim 18, wherein automatically turn on or increase the negative pressure if an abnormal breathing event is detected, and automatically maintain or turn off or decrease the negative pressure if an abnormal breathing event is not detected.

20. The method as in claim 1, wherein the negative pressure supplied is adjusted based on whether the user has abnormal breathing events.

21. The method as in claim 20, wherein automatically turn on or increase the negative pressure if an abnormal breathing event is detected, and automatically maintain or turn off or decrease the negative pressure if an abnormal breathing event is not detected.

\* \* \* \* \*